United States Patent [19]
Last et al.

[11] Patent Number: 5,290,924
[45] Date of Patent: Mar. 1, 1994

[54] RECOMBINANT PROMOTER FOR GENE EXPRESSION IN MONOCOTYLEDONOUS PLANTS

[76] Inventors: David I. Last, 19 Lindrum Crescent, Holt, ACT; Richard I. S. Brettell, 37 Cutbush Street, Kambah, ACT; Douglas A. Chamberlain, 210 Beasley Street, Farrer, ACT; Philip J. Larkin, 82 MacInnes Street, Weston, ACT; Ellen L. Marsh, 32 Ijong Street, Braddon, ACT; James W. Peacock, 16 Brassey Street, Deakin, ACT; Elizabeth S. Dennis, 100 Hopetoun Circuit, Yarralumla, ACT; Mark R. Olive, 138 Dexter Street, Cook, ACT; Jeffrey G. Ellis, 19 Roberts Street, Macquarie, ACT all of Australia

[21] Appl. No.: 51,006

[22] Filed: Apr. 21, 1993

Related U.S. Application Data

[63] Continuation of Ser. No. 525,866, May 18, 1990, abandoned, which is a continuation-in-part of Ser. No. 63,338, Jun. 15, 1987, Pat. No. 5,001,060, which is a continuation-in-part of Ser. No. 11,904, Feb. 6, 1987, abandoned, which is a continuation-in-part of Ser. No. 11,614, Feb. 6, 1987, abandoned.

[51] Int. Cl.$^5$ .................... C07H 21/04; C12N 15/00; C12N 5/00; A01H 1/04; C12R 1/41
[52] U.S. Cl. .................... 536/24.1; 435/172.3; 435/240.4; 435/252.3; 435/320.1; 800/205; 800/DIG. 55; 800/DIG. 56; 800/DIG. 57; 800/DIG. 58
[58] Field of Search .................... 536/24.1; 435/172.3, 435/252.3, 320.1, 240.4; 800/205, DIG. 55, DIG. 56, DIG. 57, DIG. 58

[56] References Cited

U.S. PATENT DOCUMENTS
5,001,060 3/1991 Peacock et al. .................... 435/172.3

OTHER PUBLICATIONS
Vasil, I. 1988. Bio/Technology 6(4):397–402.
Dennis et al. 1985. Nucleic Acids Res. 13 3):727–743.
Walker et al. 1987. Proc. Natl. Acad. Sci. USA 84:6624–6628.
Ellis et al. 1987. EMBO J. 6:11–16.
Ellis et al. 1987. EMBO J 6:3203–3208.
Peacock et al. (1987) in Plant Gene Systems and Their Biology, Alan R. Liss Inc., pp. 263–277.
Kay et al. (1987) Science 236:1299–1302.
Ow et al. (1987) Proc. Natl. Acad. Sci. USA 84:4870–4874.
Odell et al. (1985) Nature 313:810–812.
Bouchez et al. (1989) The EMBO J. 8:4197–4204.
Fromm et al. (1985) Proc. Natl. Acad. Sci. USA 82:5824–5828.
Fang et al. (1989) The Plant Cell 1:141–150.
Vasil et al. (1989) Plant Physiol. 91:1575–1579.
Last et al. (1991) Theor. Appl. Genet. 81:581–588.
Olive et al. (1990) Plant Mol. Biol. 15(4):593–604.
Rhodes et al. (1989) Biotechnology 7:548.
Shillito et al. (1989) Biotechnology 7:581–587.
Prioli et al. (1989) Biotechnology 7:589–594.
Shimamoto et al. (1989) Nature 338:274–276.
Horn et al. (1988) Plant Cell Reports 7:469–472.

*Primary Examiner*—David T. Fox

[57] ABSTRACT

A recombinant promoter molecule for enhancing expression of a plant-expressible structural gene in a monocot plant cell is provided comprising a plurality of enhancer elements selected from the group consisting of ARE and OCS elements, a truncated plant-expressible promoter, and an intron.

18 Claims, 3 Drawing Sheets

| CONSTRUCT | REGION X | | | |
|---|---|---|---|---|
| pGN | | | | |
| pIGN | | | | INTRON 1 |
| pΔ35SGN | | | | Δ 35S |
| pΔ35SIGN | | | Δ 35S | INTRON 1 |
| pΔOCSΔ35SIGN | | 4OCS | Δ 35S | INTRON 1 |
| p6AREΔADHGN | | | 6ARE | Δ ADH |
| p6AREΔADHIGN | | Δ ARE | Δ ADH | INTRON 1 |
| p6AREΔ35SGN | | | 6ARE | Δ 35S |
| p6AREΔ35SIGN | | 6ARE | Δ 35S | INTRON 1 |
| p6ARE4OCSΔADHIGN | 6ARE | 4OCS | Δ ADH | INTRON 1 |
| p35SGN | | | 35S PROMOTER | |
| p35SIGN | | 35S PROMOTER | | INTRON 1 |

FIG. 1b

FIG. 1c ΔADH

FIG. 1d Δ35S

6ARE

4OCS

RECOMBINANT PROMOTER FOR GENE EXPRESSION IN MONOCOTYLEDONOUS PLANTS

This is a continuation of co-pending application Ser. No. 07/525,866, filed on May 18, 1990, now abandoned, which is a continuation-in-part of application Ser. No. 063,338 filed on Jun. 15, 1987, now U.S. Pat. No. 5,001,060, which is a continuation-in-part of application Ser. No. 011,904 filed on Feb. 6, 1987, now abandoned, and which is also a continuation-in-part of application Ser. No. 011,614 filed on Feb. 6, 1987, now abandoned.

FIELD OF THE INVENTION

This invention relates to the field of plant molecular biology in general, and in particular to enhancer sequences and their recombined arrangement within a promoter region such that gene expression is enhanced. This invention enables the enhanced selective expression of desired structural genes in monocotyledonous plants.

BACKGROUND OF THE INVENTION

One of the most important factors to be considered in developing a plant transformation procedure is the availability of a promoter which provides reliable high level expression of introduced genes in the target cells. For example, for the transformation of plant cells with DNA encoding an antibiotic resistance marker, it is clearly desirable to obtain a high level of expression of the introduced gene to enable efficient selection of transformants. Moreover, in cases where the untransformed tissue shows a degree of natural resistance to the antibiotic, e.g., wheat and maize embryo tissue selected on kanamycin (Hauptmann et al. (1988) Plant Physiol. 86:602–606), a strong selection system would be critical for the successful production of transformed plants.

Promoters are the portions of DNA sequence at the beginnings of genes which contain the signals for RNA polymerase to begin transcription so that protein synthesis can then proceed. Eukaryotic promoters are complex, and are comprised of components which include a TATA box consensus sequence at about 35 bp 5' relative to the transcription start site, or cap site, which is defined as +1 (Breathnach and Chambon (1981) Ann. Rev. Biochem. 50:349–383; Messing et al. (1983) in *Genetic Engineering of Plants,* T. Kosuge, Meredith and Hollaender, (eds.), pp.211–227). In most instances the TATA box is required for accurate transcription initiation. Further upstream, often between −80 and −100, there can be a promoter element with homology to the consensus sequence CCAAT (Breathnach and Chambon (1981) supra. In plants the CCAAT box may be substituted by a consensus sequence which Messing et al. (1983) have termed the AGGA box, positioned a similar distance from the cap site. Additional DNA sequence in the 5' untranscribed region are believed to be involved in the modulation of gene expression. There are DNA sequences which affect gene expression in response to environmental stimuli, such as illumination or nutrient availability or adverse conditions including heat shock, anaerobiosis, or the presence of heavy metals. There are also DNA sequences which control gene expression during development, or in a tissue-specific fashion. Other DNA sequences have been found to elevate the overall level of expression of the nearby genes; such sequences have been termed "enhancers" in animal and plant systems. In yeast, similar stimulatory sequences are known which are called "upstream activating sequences," which also often appear to carry regulatory information. Promoters are usually positioned 5', or upstream, relative to the start of the coding region of the corresponding gene, and the tract containing all the ancillary elements affecting regulation or absolute levels of transcription may be comprised of less than 100 bp or as much as 1 kbp.

Among promoters that have been widely used in plant cell transformations are those of two genes encoding alcohol dehydrogenase, Adh1 and Adh2. Both Adh1 and Adh2 are induced after the onset of anaerobiosis (Freeling (1973) Mol. Gen. Genet. 127:215–227). Of the two enzymes, Adh1 is the one of primary importance during anaerobic conditions (Freeling et al. (1973) Biochem. Genet. 8:27–23). Maize Adh1 has been cloned and sequenced (dennis et al. (1984) Nucl. Acids Res. 12:3983–4000) as has been Adh2 (Dennis et al. (1985) Nucl. Acids Res. 13:727–743). Adh1 genes from other sources have also recently been cloned and sequenced (Llewellyn et al. (1987) J. Mol. Biol. 195:115–123). Howard et al. (1987) Planta 170:535–540 examined the expression of the endogenous Adh1 gene and a chimeric Adh1 gene in maize protoplasts. The Adh1 chimeric gene ADH-CAT consists of the Adh1 promoter linked to the chloramphenicol acetyltransferase (CAT) coding sequences and nopaline synthase (nos) 3' signal. ADH-CAT, introduced into maize protoplasts by electroporation, was expressed approximately four-fold higher at low oxygen concentrations than under control conditions. Expression of ADH-CAT paralleled the expression of the endogenous Adh1 gene in maize protoplasts and the anaerobic response in cell culture was qualitatively similar to the response in maize seedlings. Walker et al. (1987) Proc. Natl. Acad. Sci. 84:6624–6628 identified the sequence elements necessary for anaerobic induction of ADH-CAT based on the expression of a series of in vitro manipulated ADH-CAT chimeric genes. They showed that there is an anaerobic regulatory element (ARE) between positions −140 and −99 of the maize Adh1 promoter, and that the ARE is composed of at least two sequence elements, positions −133 to −124 and positions −113 to −99, both of which are necessary, and together are sufficient for low oxygen expression of ADH-CAT gene activity.

It was further reported (Walker et al. (1987) supra) that the Adh2 gene of maize is also regulated by anaerobiosis and contains homology to the Adh1 ARE. The homology is approximately 81% in Region I of the ARE and approximately 69% in Region II. Also, the 5'-flanking regions of the Adh genes from Arabidoosis and pea were reported to be not greater than 60% homologous to the maize Adh1 ARE over a 10 bp region.

The 35S promoter of Cauliflower Mosaic Virus (Guilley et al. (1982) Cell 30:763–773; Odell et al. (1985) supra) is one of the most frequently used promoters in plant transformation procedures. This dicot virus promoter directs expression of genes introduced into protoplasts of dicots and monocots (Fromm et al. (1985) Proc. Natl. Acad. Sci 82:5824–5828; Nagata et al. (1987) Mol. Gen. Genet. 207:242–244; Odell et al. (1988) Plant Mol. Biol. 10:263–273). Quantitative measurements of relative transcript levels in transformed tobacco cells (Morelli et al. (1985) Nature 315:200–204; Nagy et al. (1985), in *Biotechnology in Plant Science: Relevance to Agriculture in the Eighties,* M. Zaitlin, P. Day, and A. Hollaender, (eds.), Academic Press, New York, pp.

227-236) or transgenic petunia plants (Sanders et al. (1987) Nucl. Acids Res. 15:1543-1558) showed that the 35S promoter was at least 30 times stronger than the nos promoter. The strength of the 35S promoter accounts for its widespread use for high level expression of desirable traits in transgenic plants. Fang et al. (1989) The Plant Cell 1:141-150 have shown by 5', 3', and internal deletions that the −343 to −46 upstream fragment can be subdivided into three functional regions, −343 to −208, −208 to 31 90, and −90 to −46. They showed that the first two regions potentiated transcriptional activity when tested with the appropriate 35S promoter sequence. In contrast, the −90 to −46 region by itself had little activity but it played an accessory role by increasing transcriptional activity of the two distal regions.

Although, the CaMV 35S promoter is a strong promoter, driving high levels of RNA production in a wide variety of plants including plants well outside the host range of the virus, it has relatively low activity in the agriculturally significant graminaceous plants such as wheat (Lee et al. (1987) in "Progress in Plant Protoplast Research," Proceedings of the 7th International Protoplast Symposium, Wageningen, The Netherlands, Dec. 6-11, 1987, Puite et al. (eds.); Hauptmann et al. (1987) Plant Cell Rep. 6:265-270). Conversely, the monocot promoter from the Adh1 gene of maize gives very low expression in protoplasts of the dicot, Nicotiana plumbaginifolia (Ellis et al. (1987) EMBO J. 6:11-16). These observations suggest that there may be differences between monocots and dicots with respect to transcription factors and the recognition of promoter sequences.

The level of expression of a transgene can often be increased by the addition of enhancer elements, cis-acting sequences which increase the level of transcription from a promoter (Banerji et al. (1981) Cell 27:299-308). As defined by Khoury and Gruss (1983) Cell 33:313-314, an enhancer is one of a set of eukaryotic promoter elements that appears to increase transcriptional efficiency in a manner relatively independent of position and orientation with respect to the nearby gene. The prototype enhancer is found within the 72 bp repeat of SV40. It is located more than 100 bp upstream from the transcription start site, and has a consensus sequence of GTGGAAA(orTTT)G. As a rule the animal or animal virus enhancers can act over a distance as much as 1 kbp 5', in either orientation, and can act either 5' or 3' to the gene. The sequence motif is generally reiterated several times. Enhancers have been used in animal virus systems to study genes with weak promoters (Lee et al. (1981) Nature 294:228-232; Huang et al. (1981) Cell 27:245-255). There have been sequences from plant genes described which have homology to the animal enhancer consensus core sequence. Odell et al. (1985) Nature 313:810-812 have shown that sequences between −105 and −46 are required for maximal expression of the CaMV 35S promoter. Contained within that region is a sequence partially homologous to the animal enhancer core consensus sequence. It has been shown further by Bouchez et al. (1989) EMBO J. 8:4197-4204 that a 31 bp fragment from −89 to −59 of the 35S promoter contains a binding site for a nuclear protein factor present in maize and tobacco nuclei (Singh al. (1989) Proc. Natl. Acad. Sci. 86:3733-3737) and is essential for maximal activity of the promoter. Similar enhancer sequences have been found in upstream regions of the figwort mosaic virus (FMV), the carnation etched ring virus (CERV), and of seven T-DNA opine synthase genes from Ri and Ti plasmids. Ellis et al. (1987) EMBO J. 6:11-16 have shown that deletion of upstream sequences of the Adh1 promoter (from positions −1094 to −140) gave an Adh1 gene construct having only extremely low expression in transgenic tobacco. However, activity was readily detected when sequences with enhancer-like properties derived from two constitutive genes, octopine synthase (ocs) and the CaMV 35S gene, which are expressed in dicot plants, are placed upstream of the maize Adh1 promoter region. It was shown that the first 247 bp of sequence upstream of the translation initiation codon of the maize Adh1 gene confers anaerobic regulation and accurate transcription initiation to the hybrid gene in transgenic tobacco. It was further shown (Ellis et al. (1987) EMBO J. 6:3203-3208) that a 176 bp DNA sequence derived from the upstream region of the ocs promoter functions as an enhancer in protoplasts of Zea mays, a monocot plant, and Nicotiana plumbaginifolia, a dicot plant. This 176 ocs sequence was reported to function in both orientations, but its enhancing activity was found to be dependent upon its distance from the Adh1 promoter, and also to result from the presence of a 16 bp palindrome having the sequence ACG-TAAGCGCTTACGT (SEQ ID NO:6).

In other studies Kay et al. (1987) Science 236:1299-1302 reported a ten-fold higher transcriptional activity in transgenic tobacco plants with a CaMV 35S promoter containing a duplication of 260 bp of CaMV 35S upstream sequences. The duplicated region was reported also to act as a strong enhancer of heterologous promoters, increasing the activity of an adjacent and divergently transcribed transferred DNA gene several hundred fold.

It was also reported by Ow et al. (1987) Proc. Natl Acad. Sci. 84:4870-4874 that multimers of the distal region of the 35S promoter (between positions −148 and −89) were able to activate the 35S promoter core to even greater levels of expression than the native 35S promoter. It was further reported by Fang et al. (1989) supra that monomers and multiples of an upstream 35S promoter fragment (−209 to −46) can act as enhancers to potentiate transcription from a heterologous promoter. In these studies eight copies of the upstream region between positions −209 to −46 of the 35S promoter were cloned at position −50 of the rbcS−3A (small subunit of the ribulose bisphosphate carboxylase) gene; the octamer increased the rbcS−3A transcript to a level even higher than that obtained with the rbcS−3A upstream region (Fang et al. (1989) supra).

Enhancers obtained from sources such as viral or bacterial genomes were shown to function in enhancement of expression in plants of a desired gene. In one such case, the species-specificity of a promoter was modified by the addition of the octopine synthase (OCS) enhancer from *Agrobacterium tumefaciens* to the maize Adh1 promoter (Ellis et al. (1987) EMBO J. 6:11-16). After addition of the OCS enhancer, the maize Adh1 promoter is able to give strong anaerobically inducible expression in transgenic tobacco plants. In another case, it was reported that when the OCS enhancer is placed directly adjacent to the ARE, the OCS-ARE construct shows maximal expression in maize protoplasts and CAT expression is not further increased by anaerobic stress (Peacock et al. (1987) in *Plant Gene Systems and Their Biology*, Alan R. Liss, Inc., pp. 263-277). It was also reported (Callis et. al. (1987) Genes and Dev. 1:1183-1200) that the inclusion of the maize Adh1 Intron 1 downstream of the Adh1 promoter in the untranslated leader has been shown to increase expression ten-fold from a chloramphenicol acetyltransferase (CAT) marker gene introduced into maize protoplasts.

SUMMARY OF THE INVENTION

A primary object of this invention is to provide a recombinant promoter molecule which will enable those skilled in the art to obtain reliable high levels of expression of introduced genes in target cells. This object is to be accomplished by utilizing combinations of enhancer sequences from the 5' untranscribed regions of plant-expressible genes. In the preferred embodiment, enhancer sequences are derived from the upstream region of the maize alcohol dehydrogenase 1 (Adh1) gene and the octopine synthase gene and, most preferably, comprise a plurality of or a combination of enhancer elements, e.g., comprising the anaerobic regulatory element (ARE) (SEQ ID NO:3), the octopine synthase element (OCS) (SEQ ID NO;1) and the Intron 1 from the Adh1 gene (SEQ ID NO:5).

It is another object of this invention to provide an improved promoter construct which will give ten to fifty-fold higher expression of an introduced marker gene in monocot suspension cell protoplasts than is obtained with the Cauliflower Mosaic Virus 35S (CaMV 35S) promoter. It is preferred that the recombinant promoter molecule of this invention contain multiple copies of the ARE grouped together in either a spaced or adjacent relation to each other, and multiple copies of OCS element grouped together in either a spaced or adjacent relation to each other. It is more preferred that the ARE elements be positioned 5' to the OCS element and that the ARE and OCS elements be positioned 5' to the TATA box region. In an exemplified embodiment, the improved promoter construct for monocots comprised six tandemly repeated copies of the ARE of the maize Adh1 gene, four tandemly repeated copies of the OCS element (SEQ ID NO:1) from the octopine synthase gene of Agrobacterium tumefaciens (OCS), the TATA box region from a plant-expressible promoter, an intron which is part of the untranslated leader of a plant-expressible gene, e.g. Intron 1 (part of the untranslated leader from nucleotide +119 to +672) of the maize Adh1 gene, a plant-expressible structural gene, e.g., the E. coli β-glucuronidase gene (GUS) and a plant-expressible termination signal, e.g., the nos terminator from the nopaline synthase gene of Agrobacterium tumefaciens.

Another object of this invention is to provide an improved promoter construct which will give enhanced expression of marker genes over the CaMV 35S promoter in monocot cells, e.g., approximately about a sixteen-fold enhancement in barley; and seven- to ten-fold higher expression of marker genes than the CaMV 35S promoter in protoplasts of dicot cells. It is preferred that the recombinant promoter molecule contain multiple copies of the OCS element which are positioned in a spaced or adjacent relation to each other. In an exemplified embodiment, the improved promoter construct comprised four tandemly repeated copies of the OCS (SEQ ID NO;1), a TATA box region from a plant-expressible promoter, e.g. a truncated CaMVΔ35S promoter (deleted to nucleotide −90) (SEQ ID NO:2), an intron which is part of the untranslated leader of a plant-expressible gene, e.g. Intron 1 (SEQ ID NO:5) from the maize Adh1 gene, a plant-expressible structural gene, e.g. the GUS coding region, and a plant-expressible termination signal, e.g. the nos terminator from the nopaline synthase gene of Agrobacterium tumefaciens.

It is also an object of this invention to enable the development of an effective selection system for transformed plant cells. Such an improved selection system is based on a reliable enhancement in expression of structural genes in transgenic tissues. For example, the recombinant promoter constructs provided by this invention, when linked to an antibiotic resistance gene, are useful for generating an increased level of antibiotic resistance for selection during transformation.

Another object of this invention is to provide a recombinant promoter construct designed to exhibit high level, tissue specific expression in plants. In an exemplified embodiment, the p40CSΔ35SIGN construct of this invention showed superior utility for leaf specific expression.

This invention also provides a method for obtaining high level expression of desired genes in monocot plant cells. Such desired plant-expressible genes, as known to those skilled in the art include the crystal toxin protein gene of Bacillus thuringiensis, glyphosate resistance genes, modified seed storage protein genes and the like. This method involves the construction of a recombinant promoter molecule which, in an exemplified embodiment, comprises multiple AREs and/or multiple OCS elements positioned 5' to a plant-expressible truncated promoter providing a TATA box region and optionally, followed in the 3' direction by the Intron 1 (SEQ ID NO:5) of the maize Adh1 gene, a plant-expressible structural gene (e.g., the GUS gene) and the nos terminator from the nopaline synthase gene of Agrobacterium tumefaciens. In a preferred embodiment, six copies of ARE (SEQ ID NO:3) and four copies of OCS (SEQ ID NO:1) were employed in the constructions of promoter constructs.

It is another object of this invention to provide a method of rendering an inducible gene constitutive with respect to regulation of gene expression. In an exemplified embodiment of this invention, the Adh1 promoter, which normally functions in response to anaerobiosis, is designed with enhancer elements and enabled to show high level gene expression in a constitutive manner.

The construction of recombinant promoter molecules is accomplished by conventional techniques using plant enhancer fragments as described above. Further, the construction of such DNA molecules can employ specific sequences from known genes as described herein or functionally equivalent sequences from other sources which have been shown to confer enhancement of expression of heterologous genes placed under their regulatory control, e.g. the 780 T-DNA enhancer. Other truncated plant-expressible promoters, instead of the truncated Adh1 promoter (SEQ ID NO:4) and the truncated CaMVΔ35S promoter (SEQ ID NO:2), can be employed to provide the necessary TATA box sequences in these constructions. Any plant-expressible structural gene can be used in these constructions.

After construction, the recombinant DNA expression system comprising an improved promoter molecule as described herein is introduced into plant tissue so that the enhancer elements/truncated promoter/structural gene combinations are expressed at high levels in the desired plant tissue, preferably in monocot tissue. Transformation of plant cells and tissues with foreign DNA can be achieved in a number of ways known to the art. In an exemplified embodiment, the technique of electroporation was used.

The method of the present invention is generally applicable to the expression of structural genes in both monocotyledonous and dicotyledonous plants. This method, utilizing a promoter constructed for monocots, is particularly applicable to the family Graminaceae, in particular to maize and wheat.

Other objects of this invention are plants, plant cells and plant tissues containing the recombinant promoter molecules described herein. Further objects are vectors and expression cassettes comprising the said recombinant promoter molecules, and bacterial cells comprising such vectors suitable for maintenance, replication and plant transformation.

BRIEF DESCRIPTION OF THE FIGURES

FIGS. 1a through 1f are schematic representations of the DNA combinations used in the construction of different recombinant promoter molecules. (1a) Generalized plasmid used for assaying promoter activities of promoter regions X. (1b) Structures of promoter regions X in the different constructs. (1c) ΔADH promoter (SEQ ID NO:4): TATA box and transcription start site are indicated. There are no ATG translation starts downstream of the transcription start site. (1d) Δ35S promoter(SEQ ID NO:2) TATA box and ocs-element are indicated. (1e) 6ARE element: Regions I and II of each ARE (positions −140 to −99 in the maize Adh1 gene) are indicated. The element consists of one ARE (SEQ ID NO:3) in the natural orientation preceded by five AREs in the reverse orientation. (1f) 4OCS element: The element contains four 40 bp direct repeats of the −211 to −172 region (SEQ ID NO:1) from the Ocs gene. All base numbering in (1c) to (1f) indicates the natural positions of bases in the sequences of the genes from which the constructs were derived.

DETAILED DESCRIPTION OF THE INVENTION

Figure 1A:
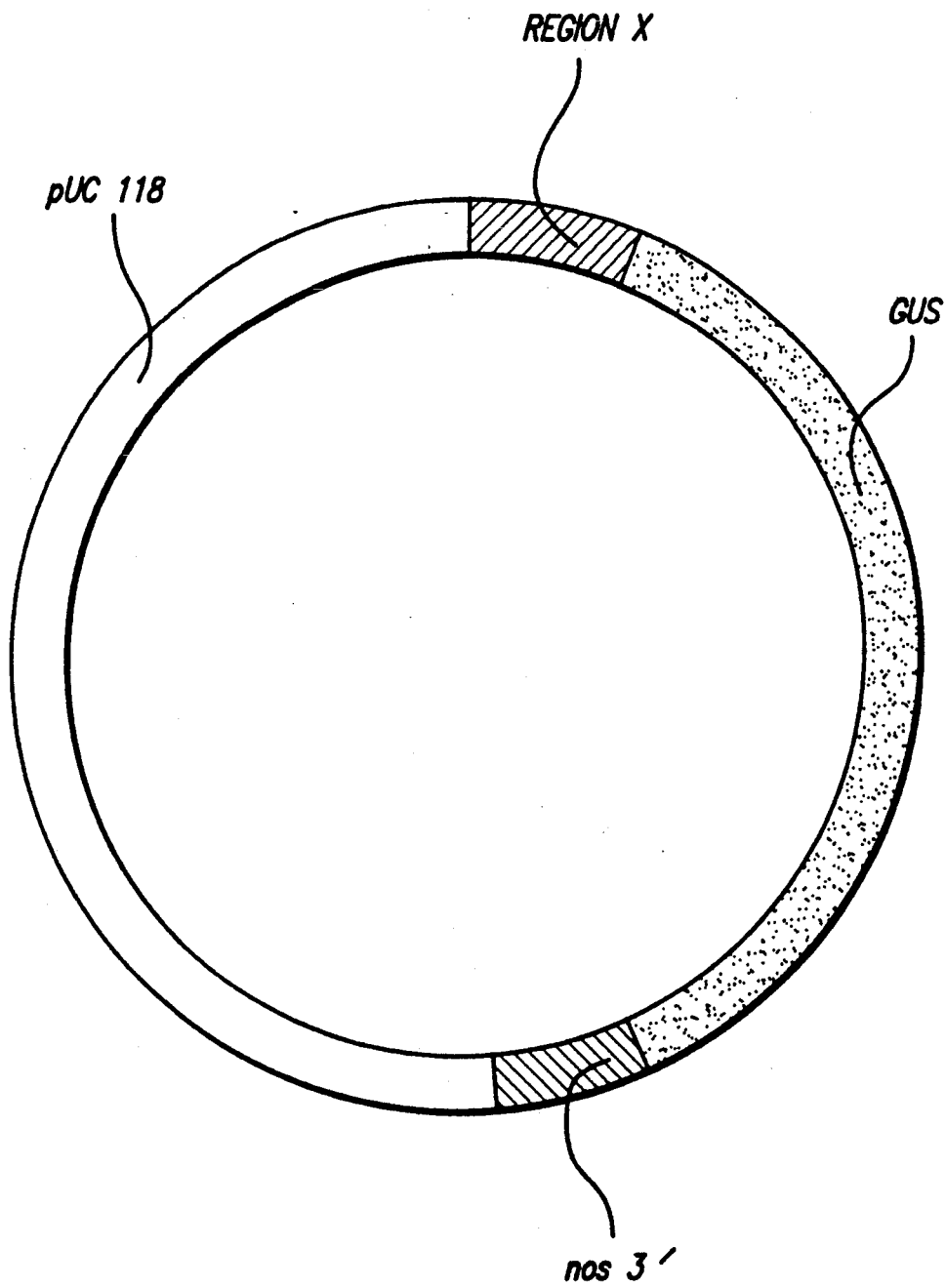

The following definitions are provided in order to remove ambiguities in the intent or scope of their usage in the Specification and claims.

Expression refers to the transcription and translation of a structural gene so that a protein is synthesized.

A promoter refers to the sequences at the 5′ end of a structural gene which direct the initiation of transcription. Promoter sequences are necessary, but not always sufficient, to drive the expression of a downstream gene. Eukaryotic promoters generally contain a sequence with homology to the consensus 5′-TATAAT−3′ (TATA box) about 10-35 bp 5′ to the transcription start (cap) site, which is by convention numbered +1; bases 3′ to the cap site are given positive numbers while bases 5′ to the cap site receive negative numbers reflecting their distances from the cap site. About 30-70 bp 5′ to the TATA box there is often another promoter component with homology to the canonical form 5′-CCAAT-3′ (R. Breathnach and P. Chambon (1981) Ann. Rev. Biochem. 50:349-383). In plants the CCAAT "box" is sometimes replaced by the AGGA "box" (Messing et al. (1983) in *Genetic Engineering of Plants*, T. Kosuge et al. (eds.), Plenum Press, pp. 211-227). Other sequences conferring tissue specificity, response to environmental signals or maximum efficiency of transcription may be found interspersed with these promoter elements or found further in the 5′ direction from the cap site. Such sequences are often found within 400 bp of the cap site, but may extend as far as 1000 bp or more.

A truncated promoter refers to the TATA box region comprising proximal sequences necessary for initiating transcription but excluding enhancer sequences. In this invention it is contemplated that a truncated promoter comprises the region between approximately 200 bp 5′ and approximately 200 bp 3′ from the cap site (+1), and more preferably the region between approximately 100 bp 5′ and approximately 110 bp 3′ from the cap site.

ADH refers generally to a plant-expressible alcohol dehydrogenase gene and, specifically, to the alcohol dehydrogenase gene from maize.

Adh1 promoter refers to the DNA fragment spanning the region between nucleotide positions about −1094 and about −106 of the alcohol dehydrogenase gene 1 from maize, or a homologous fragment that is functionally equivalent. The sequence is numbered with the cap site designated as +1 according to the correction published by Ellis et al. (1987) supra.

Δ preceding the symbol for a promoter (such as ΔADH for the Adh promoter or Δ35S for the 35S promoter) means that the promoter is truncated as defined herein.

ΔADH refers generally to a truncated plant-expressible Adh promoter providing the TATA box sequences necessary for initiating transcription, and specifically to the truncated Adh1 promoter from the Adh1 gene of maize spanning the DNA region from about nucleotide −100 to about nucleotide +106 (SEQ ID NO:4), as described by Ellis et al. (1987b) supra, or a homologous fragment that is functionally equivalent.

Δ35S refers generally to a truncated, plant-expressible CaMV promoter providing the TATA box sequences necessary for initiating transcription, and specifically to the truncated 35S promoter from the Cauliflower Mosaic Virus (CaMV) 35S gene spanning the DNA region from about nucleotide −90 to about nucleotide +3, or a homologous fragment that is functionally equivalent. The region between nucleotides about −90 and about −45 in the CaMV 35S promoter contains an OCS element (Bouchez et al. (1989) supra).

ARE or ARE element refers to the anaerobic regulatory element as defined by Walker et al. (1987) supra, or a homologous fragment that is functionally equivalent. The ARE fragment from the maize Adh1 gene spans a DNA region between nucleotide positions −140 and −99 (SEQ ID NO:3). The ARE is composed of at least two sequence elements, positions −133 to −124 and positions −113 to −99, both of which are necessary and together are sufficient for low oxygen expression of Adh-CAT gene expression (Walker et al. (1987) supra). The DNA sequences of Regions I and II must contain 5′-GGTTT-3′, and probably must contain 5′-TGGTTT-3′. In this invention, it is contemplated that an ARE may consist of only Region I to the exclusion of Region II. Further, it is contemplated that functional plant ARE elements can be derived from anaerobically induced genes from alternate sources, which include, but are not limited to, sequences from the upstream regions of the genes for maize Adh1 and Adh2 and maize aldolase.

OCS or OCS element refers to the 40 bp sequence from −211 to −172 (SEQ ID NO:1) taken from the 176 bp ocs enhancer fragment, spanning nucleotide positions −292 to −116, of the octopine synthase gene that was used to enhance the expression of the maize Adh1 promoter in transgenic tobacco (Ellis et al. (1987)

EMBO J. 6:11-16 and (1987) EMBO J. 6:3203-3208), or a homologous fragment that is functionally equivalent. The OCS comprises a 16 bp palindromic sequence, 5'-ACGTAAGCGCTTACGT-3', (SEQ ID NO:6) that is an essential component of the ocs enhancer. The OCS element occurs between nucleotides −193 and −178 of the octopine synthase gene from *Agrobacterium tumefaciens*. The presence of sequences homologous and functionally equivalent to the OCS element have been identified in other sources (Bouchez et al. (1989) supra). It is contemplated that the OCS element employed in this invention also comprises sequences from other sources that show at least about 50% homology and functional equivalence (Bouchez et al. (1989) supra) to the OCS element of Ellis et al. (1987) EMBO J. 6:3203-3208.

I in a promoter enhancer element designation stands for Intron.

Intron refers generally to a nucleotide sequence naturally found as an intron positioned between the transcription start site and the translation start site in a plant-expressible gene. The intron specifically used in the Examples hereof is a 557 bp fragment from Intron I of the maize Adh1 gene spanning nucleotides 119 to 672 (nucleotide numbering as per Dennis et al. (1984) Nucl. Acids Res. 12:3983-4000) (SEQ ID NO:5), or a homologous fragment that is functionally equivalent.

Emu or Emu cassette refers to an expression cassette consisting of the '6ARE4OCSΔADHI' construct.

pEmuGN is the abbreviation for the p6ARE4OCS-ΔADHIGN construct.

G refers to the *E. coli* β-glucuronidase gene.

N refers to the transcription termination signal sequences from the nopaline synthase gene.

High level of expression refers to expression of a desired gene under control of a recombinant promoter of this invention that is at least about 10- to 50-fold higher in a monocot cell, than is obtained under control of the CaMV 35S promoter in the same plant system.

Regulatory control refers in general to the modulation of gene expression induced by DNA sequence elements, particularly those located upstream of (5' to) the transcription start site. Regulation may be analogous to an off/on switch which responds to environmental conditions, or regulation may result in variations in the level of gene expression. For example, the anaerobic regulatory element functions in such a way that downstream gene expression results only when environmental conditions are anaerobic. Experimental anaerobiosis refers to an atmosphere containing 5% oxygen/95% nitrogen to which plant tissue, cultured cells or protoplasts are subjected.

Placing a structural gene under the regulatory control of a promoter or a regulatory sequence element means positioning the structural gene such that the expression of the gene is controlled by these sequences. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art and demonstrated herein with multiple copies of regulatory elements, some variation in this distance can occur.

A structural gene is that portion of a gene comprising a DNA segment encoding a protein, polypeptide or a portion thereof. The term can refer to copies of a structural gene naturally found within the cell, but artificially introduced, or the structural gene may encode a protein not normally found in the plant cell into which the gene is introduced, in which case it is termed a heterologous gene. A heterologous structural gene may be derived in whole or in part from a bacterial genome or episome, eukaryotic genomic or plastid DNA, cDNA, viral DNA, or chemically synthesized DNA. It is possible that a structural gene may contain one or more modifications in either the coding or the untranslated regions which could affect the biological activity or the chemical structure of the expression product, the rate of expression, or the manner of expression control. Such modifications include, but are not limited to, mutations, insertions, deletions, and substitutions of one or more nucleotides. The structural gene may constitute an uninterrupted coding sequence or it may include one or more introns, bounded by the appropriate plant-functional splice junctions. The structural gene may be a composite of segments derived from a plurality of sources, naturally occurring or synthetic. The structural gene may also encode a fusion protein, so long as the experimental manipulations maintain functionality in the joining of the coding sequences.

Homologs of structural genes, enhancer or regulatory sequences, or other sequences are homologous sequences that are functionally equivalent thereto, and have at least 50% homology thereto. Such sequences may be identified by those skilled in the art by the ability of their nucleic acids to cross-hybridize under conditions of appropriate stringency as is well understood in the art (as described in Hames and Higgins (eds.) (1985) *Nucleic Acid Hybridisation*, IRL Press, Oxford, UK). It will be understood that there may be minor sequence variations within sequences or fragments used or disclosed in this application. These variations may be determined by standard techniques to enable those of ordinary skill in the art to manipulate and bring into utility the functional units of the regulatory elements, the promoter elements necessary to direct the initiation of transcription, and the structural gene followed by a plant-expressible transcription termination (and perhaps polyadenylation) signal.

For example, the OCS element was first isolated as an enhancer element in the promoter of the ocs gene where it was identified as a 16 bp palindromic sequence (SEQ ID NO:6) (Ellis et al. (1987) EMBO J. 6:11-16). The transcriptional enhancing activity of the OCS element correlated with in vitro binding of a transcription factor. OCS elements were also identified in the promoter regions of six other T-DNA genes involved in opine synthesis and three plant viral promoters including the CaMV 35S promoter (Bouchez et al. (1989) supra). These elements were shown to bind the ocs transcription factor in vitro and enhance transcription in plant cells. Comparison of the 20 bp nucleotide sequences of these ten elements (which show at least about 50% homology to the OCS element first identified in the ocs gene) has defined a 20 bp consensus sequence, TGACG(T/C)AAG (C/G)(G/A)(A/C)T(G/T)ACG(T/C)(A/C)(A/C) (SEQ ID NO:7), which includes the 16 bp palindrome in its center. In this invention it is contemplated that the OCS element is exemplified by, among others, any of the ten enhancer elements identified above in Bouchez et al. (1989) supra, the consensus sequence and nucleotide sequences having 50% homology to the OCS element first identified in the ocs gene described by Ellis et al. (1987) EMBO J. 6:11-16. It is further contemplated in this invention that DNA fragments showing at least about 50% homology to the ARE element first described in the maize Adh1 gene show functional equivalence to the ARE element and can be used in place of an ARE element in recombinant promoter constructs.

Plant tissue includes differentiated and undifferentiated tissues of plants, including, but not limited to, roots shoots, leaves, pollen, seeds, tumor tissue, and various forms of cells in culture, such as single cells, protoplasts, embryos and callus tissue. The plant tissue may be in planta or in organ, tissue or cell culture.

Production of genetically modified plant tissue expressing a structural gene under the control of regulatory elements and a downstream promoter combines the teachings of the present disclosure with a variety of techniques and expedients known in the art. In most instances alternate expedients exist for each stage of the overall process. The choice of expedients depends on variables such as the plasmid vector system chosen for the cloning and introduction of the recombinant DNA molecule, the plant species to be modified, the particular structural gene, promoter elements and the regulatory elements used. Persons skilled in the art are able to select and use appropriate alternatives to achieve functionality. Culture conditions for expressing desired structural genes in cultured cells are known to the art. Also as in known to the art, a number of both monocotyledonous and dicotyledonous plant species are transformable and regenerable, such that whole plants containing and expressing desired genes under regulatory control of the promoter molecules of this invention may be obtained. As is known to those skilled in the art, expression in transformed plants may be tissue-specific and/or specific to certain developmental stages. Truncated promoter selection and structural gene selection are parameters which may be optimized to achieve desired plant expression, all as known to those skilled in the art and as taught herein.

This invention is based in part on the discovery by Applicants that replacement of part of the maize Adh1 promoter from position −35 to +106 with the CaMVΔ35S promoter truncated to position −45 gave a hybrid promoter which retained the anaerobic regulation of the parent gene when assayed in maize protoplasts. However, if a CaMVΔ35S promoter truncated to −90 (SEQ ID NO:2) was used instead, expression was again constitutive. The region between −90 and −45 in the CaMVΔ35S promoter was shown to contain an OCS element (Bouchez et al. (1989) supra), a 20 bp consensus sequence containing a 16 bp palindrome originally identified in the OCS enhancer fragment (Ellis et al. (1987) EMBO J. 6:3203-3208). Thus, the coupling of the OCS element from either the CaMVΔ35S promoter or a fragment of the ocs gene together with the maize Adh1 promoter upstream region gives a construct which is constitutively expressed in maize cells.

It was further found that the array of four tandemly repeated OCS elements (SEQ ID NO:1) (4OCS) had stronger activity than a single OCS element in enhancing expression of a CAT gene driven by the Adh1 promoter. Similarly, replacing the single ARE in the maize Adh1 promoter with 6 tandemly repeated ARE, was shown to give an eleven-fold increase in expression under anaerobic conditions.

In this invention, a number of DNA constructs were prepared to enable high levels of expression of structural genes in plant cells. A series of promoters were constructed (see FIG. 1) based on either a truncated maize Adh1 promoter (spanning nucleotides −100 to +106 (SEQ ID NO:4), Ellis et al. (1987) EMBO J. 6:3203-3208) or a truncated 35S promoter (spanning nucleotides −90 to +3) (SEQ ID NO:2). Various combinations of OCS elements (SEQ ID NO:1) and AREs (SEQ ID NO:3) were added upstream in an attempt to make a highly expressing promoter. Additionally, a fragment containing the Intron 1 (SEQ ID NO:5) of the maize Adh1 promoter was inserted between the promoter and the structural gene in some of the constructs.

The relative strengths of the recombinant promoters were assessed in protoplasts of one dicot and four monocot cell lines by assaying the product of the reporter gene, e.g., GUS enzyme activity, 44-48 hours after the DNA constructs were introduced into the plant protoplasts by electroporation. The results presented in Table 1 were normalized by taking the value for p35SGN to be 1.0. This normalization reduced the variation observed between experiments carried out on different protoplast preparations. Values shown are means of at least five and up to eight replica experiments using protoplasts from at least three different isolations. The range of specific activities of GUS produced using p35SGN, p4OCSΔ35SIGN and p6ARE-4OCSΔADHIGN are shown in Table 2. Although in many cases the values of GUS specific activity varied considerably between replicates, their ranking order was generally the same between replicates within each plant species. Relative expression levels were not dependent on the selection of a desired structural gene. It is emphasized that the standard conditions in this study employed a relatively low amount of DNA ($1.2\mu g/10^5$ protoplasts). It was found that this concentration of DNA gave the clearest differential response in GUS enzyme activity between different constructs. Higher GUS activities were observed for some of the less efficient constructs when the DNA concentrations were increased.

As shown in Table 1, in all monocot cell lines tested, e.g., maize, wheat, einkorn (*Triticum monococcum*), lolium (*Lolium multiflorum*) and rice, the CaMVΔ35S promoter showed weak expression; the marker GUS gene expression was comparable to that recorded for the "promoter-less" constructs pGN and pIGN. In general, constructs based on the truncated Adh1 promoter were expressed more highly in monocots than those based on the truncated CaMVΔ35S promoter. A consistently high level of expression in the monocot cell lines was given by those constructs in which six ARE elements (SEQ ID NO:3) were linked to the maize Adh1 promoter (SEQ ID NO:4) in the presence of the maize Adh1 Intron 1. The construct p6ARE4OCS-ΔADHIGN, which includes additionally four copies of the OCS element (SEQ ID NO:1), showed the highest expression in all the monocot cell lines. This plasmid gave a ten- to fifty-fold increase in GUS expression over the CaMVΔ35S promoter in suspension cell protoplasts of the monocots. The high expression obtained with this construct most probably resulted from several factors. The use of the monocot TATA box from the maize Adh1 gene undoubtedly made a positive contribution. The untranslated leader from the maize Adh1 gene is long (106 bases) in this construct, a factor which may also be important, as deletion of the leader sequence from the 3' end beyond position +80 in the maize Adh1 gene was shown to abolish expression in many systems. In general, the constructs based on ΔADH (SEQ ID NO:4) performed better than those based on Δ35S (SEQ ID NO:2) in the monocot cell lines. Conversely, the Δ35S-based promoters out-performed the ΔADH-based promoters in the dicot (Nicotiana plumbaginifolia) cell line. Inclusion of the maize Adh1 Intron 1 (SEQ ID NO:5) gave an increase in expression with p6AREΔADHIGN and p6ARE4OCSΔADHIGN, but no effect of the intron was observed in the CaMVΔ35S promoter-based constructs. In the case of the "promoterless" constructs, pGN gave no detectable GUS expression above the background observed for protoplasts electroporated in the absence of DNA. However, pIGN, which includes the maize Adh1 Intron 1(SEQ ID NO:5), gave a low measurable GUS activity.

Another important factor contributing to the high level of expression obtained from p6ARE4OCSΔADHIGN, was the presence of multiple copies of OCS elements (SEQ ID NO:1) and AREs (SEQ ID NO:3). The OCS element is a strong enhancer which has been shown to function in both dicots and monocots (Ellis et al. (1987) EMBO J. 6:3203-3208) and addition of five extra copies of the ARE (SEQ ID NO:3) increased expression from the maize Adh1 promoter when assayed in maize protoplasts. The GUS marker gene can be replaced with the coding regions of other plant-expressible structural genes. Hence, the cassette '6ARE4OCSΔADHI' is useful where a high level of gene expression is required in cultured monocot cells. The '6ARE4OCSΔADHI' cassette has been code named the 'Emu' cassette and, accordingly, the p6ARE4OCSΔADHIGN construct has been abbreviated to pEmuGN.

The plasmid p6ARE4OCSΔADHIGN was shown by the inventors to be anaerobically-inducible in maize. Anaerobically-induced cells showed a greater than 10-fold increase in expression over aerobically grown cells. The pEmuGN construct of this invention gave a higher level of expression than p6AREΔADHIGN, as documented in Table 2. This suggested that addition of the OCS elements to promoter constructs allows the attainment of expression levels equal to the anaerobically induced level, even under anaerobic conditions. This suggestion was characterized further. The anaerobic inducibilities of pEmuGN, p6AREΔADHIGN and p6AREΔ35SIGN were determined using wheat (L1) protoplasts. Some samples were incubated in air at 25° C. (aerobic) with shaking whilst others (referred to as 'anaerobically-induced') were placed in a 5%O$_2$/95%N$_2$ atmosphere and shaken at 25° C. for the duration of the incubation (44 to 48 hours). As shown in Table 3, p6AREΔADHIGN was anaerobically induced about three-fold in wheat (L1) protoplasts. On the other hand, pEmuGN gave a similar level of expression under both anaerobic and aerobic conditions, which was greater than the fully induced expression from p6AREΔADHIGN. Thus, the addition of the 4OCS element to p6AREΔADHIGN overrides the requirement for anaerobic induction. The analog of p6AREΔADHIGN in which ΔADH (SEQ ID NO:4) was replaced by Δ35S (SEQ ID NO:2) (p6AREΔ35SIGN) did not give a high enough level of expression to allow any inferences concerning its anaerobic inducibility.

As shown by the results presented in Table 1, the addition of the 4OCS element to the truncated promoter Δ35SIGN construct greatly increased expression in Nicotiana plumbaginifolia protoplasts. The promoter in this construct is useful where a high level of gene expression is required in dicots. The presence of the maize Adh1 Intron 1 (SEQ ID NO:5) in this and other highly expressed constructs indicated that successful splicing of the maize intron takes place in Nicotiana. A version of p4OCSΔ35SIGN without the intron (p4OCS'35SGN) gave a similarly high level of expression, showing that the presence of the intron is not required for high level of expression in Nicotiana. Constructs based on the truncated Adh1 promoter gave little or no expression in Nicotiana, except in the case of pEmuGN, which contains the 4OCS element, and which gave a similar level of expression to that given by the 35S promoter.

Differences were noted between the relative performances of certain constructs in different cell lines. The construct pEmuGN gave a two-fold increase in expression over p6AREΔADHIGN in wheat, einkorn and rice, but in maize this ratio was five-fold and in Lolium multiflorum it was sixteen-fold, which is close to the value obtained for Nicotiana plumbaginifolia (seventeen-fold). It is also observed that the construct giving the highest expression in Nicotiana (p4OCSΔ35SIGN) is also relatively highly expressed in Lolium (44% of the expression obtained with pEmuGN) whereas the corresponding value for wheat is less than 1%. These differences probably reflect different complements of transcription factors in the different cell lines. The Lolium cell line may lie somewhere between the wheat and the Nicotiana cell lines in this respect.

The relative strengths of the different promoter constructs were also tested in leaf tissue, e.g., in mesophyll protoplasts of barley (Hordeum vulgare). As shown in Table 2, the barley mesophyll protoplasts required slightly different electroporation conditions than did the other cells. For this reason, the absolute values obtained for barley are not strictly comparable with those obtained for the cell lines, although it is clear that the relative levels of expression from the different promoters do differ markedly from those observed in the established cell lines. The construct pEmuGN gave no expression. The only construct that gave a level of expression significantly above background was p4OCSΔ35SIGN. This construct gave a high level of expression in barley mesophyll protoplasts comparable to that observed with pEmuGN in the suspension cell protoplasts. This result suggests that pEmuGN would not be highly expressed in monocot mesophyll tissue. In maize, the Adh1 gene is not expressed in leaf tissue, suggesting that leaves may not contain the necessary transcription factors.

The recombinant DNA molecule carrying the desired structural gene under the regulatory control of regulatory elements may be introduced into plant tissue by various techniques known to those skilled in the art. The technique used for a given plant species or specific type of plant tissue depends on the known successful techniques. Means for introducing recombinant DNA into plant tissue include, but are not limited to, transformation (Paszkowski et al. (1984) EMBO J. 3:2717-2722), electroporation (Fromm et al. (1985) Proc. Natl. Acad. Sci. USA 82:5824-5828), or microinjection of the DNA (Crossway et al. (1986) Mol. Gen.

Genet. 202:179–185) or T-DNA-mediated transfer from *Agrobacterium* to the plant tissue. Representative T-DNA vector systems are described in the following references: An et al. (1985) EMBO J. 4:277–284; Herrera-Estrella et al. (1983) Nature 303:209–213; Herrera-Estrella et al. (1983) EMBO J. 2:987–995; Herrera-Estrella et al. (1985) in *Plant Genetic Engineering*, Cambridge University Press, New York, pp. 63–93. Once introduced into the plant tissue, the expression of the structural gene may be assayed in a transient expression system, or it may be determined after selection for stable integration within the plant genome. Techniques are known for the in vitro culture of plant tissue, and in a number of cases, for regeneration into whole plants. Procedures for transferring the introduced gene from the originally transformed plant into commercially useful cultivars are known to those skilled in the art.

Except as noted hereafter, standard techniques for cloning, DNA isolation, amplification and purification, for enzymatic reactions involving DNA ligase, DNA polymerase, restriction endonuclease and the like, the PCR technique and various separation techniques are those known and commonly employed by those skilled in the art. A number of standard techniques are described in Maniatis et al. (1982) *Molecular Cloning*, Cold Spring Harbor Laboratory, Cold Spring Harbor, N.Y.; Wu (ed.) (1979) Meth. Enzymol. 68; Wu et al. (1983) Meth. Enzymol. 100 and 101; Grossman and Moldave (eds.) (1980) Meth. Enzymol. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Method in Molecular Biology;* Glover (ed.) (1985) *DNA Cloning* Vol I and II, IRL Press, Oxford, UK; Hames and Higgins (eds.) (1985) *Nucleic Acid Hybridisation*, IRL Press, Oxford, UK; Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

It is understood in the art that modifications may be made to the structural arrangement and specific enhancer and promoter elements of the recombinant promoter molecule described herein without destroying the improved enhancing activity of gene expression. For example, it is contemplated that a substitution may be made in the choices of plant-expressible enhancer and promoter elements without significantly affecting the function of the recombinant promoter molecule of this invention. Further, it is contemplated that nucleotide sequences homologous to the active enhancer elements utilized herein may be employed advantageously, either as a substitution or an addition to the recombinant promoter construct for improved gene expression in plant cells.

Applicants have shown that a high level of gene expression can be obtained using a plurality of enhancer elements in combination with truncated promoters in plant species including both monocots and dicots. Selection of appropriate elements to optimize expression in any particular species is a matter of ordinary skill in the art utilizing the teachings of this disclosure, e.g., the guidance provided in the tables hereof. It will also be understood that optimization of gene expression also results from the arrangement, orientation and spacing of the different enhancer elements as well as the multiple copies of a particular element with respect to one another, and with respect to the position of the TATA box, as will be apparent to those skilled in the art using the teachings of this disclosure.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the functional features of the recombinant promoter molecules described herein and how to employ those alternatives to achieve functional equivalents of the recombinant promoter molecules of the present invention. It is intended that the present invention include those variants, modifications, alternatives and equivalents which are appreciated by the skilled artisan and encompassed by the spirit and scope of the present disclosure.

The following Examples are provided for illustrative purposes only and are not intended to limit the scope of the invention.

EXAMPLES

Example 1.

Construction of plasmids containing hybrid promoters

Standard molecular biological techniques were carried out according to Maniatis et al. (1982) Molecular Cloning: a Laboratory Manual. Cold Spring Harbor Laboratory, Cold Spring Harbor, N.Y. All plasmids utilized in the invention can be prepared according to the directions of the Specification by a person of ordinary skill in the art without undue experimentation employing materials readily available in the art.

(a) p35SGN, p35SIGN, pGN and pIGN constructs

The plasmid p35SGN was derived by ligating the 800 bp HindIII/EcoR1 fragment from pBI121 containing the CaMVΔ35S promoter driving the β-glucuronidase (GUS) gene linked to the NOS 3′-termination signal (Jefferson et al. (1987) EMBO J. 6:3901–3907) into pUC118 (Vieira and Messing (1987) Methods Enzymol. 153:3–11). To construct p35SIGN, a 557 bp fragment from Intron 1 of the maize Adh1 gene spanning nucleotides 119 (BclI) to 672 (Bal31 - deleted) was end-filled with the Klenow fragment of Escherichia coli DNA polymerase and cloned into the SmaI site in pBI121. In p35SIGN the CaMVΔ35S promoter (SEQ ID NO:2), Intron 1, (SEQ ID NO:5), Gus gene and nos 3′-termination signals were sub-cloned as a single HindIII-EcoRI fragment into pUC118.

To produce the promoterless control plasmid, pIGN, the intron 1-GUS-NOS-fragment in p35SIGN (BamH1-EcoR1) was cloned into pUC118. The plasmid pGN was derived from pIGN by replacement of the BamH1/SacI fragment containing intron 1 of maize Adh1 and GUS by the BamH1/SacI 'GUS' fragment from p35SGN.

(b) pΔ35SGN and pΔ35SIGN constructs

Plasmids pΔ35SGN and pΔ35SIGN were derived from pGN and pIGN by addition of the Sal1/BamH1 'Δ35S' fragment from pΔ35S(−90). The parent plasmid, p35SCN was fully described in Walker et al. (1987) Proc. Natl. Acad. Sci. 84:6624–6628. A Sal1 linker was inserted into the EcoRV site (nucleot 7665) of the CaMVΔ35S promoter in p35SCN at position −90; the Sal1 to Hind111 fragment containing the truncated 35S promoter fragment, CAT gene and 3'-termination signal was subsequently cloned into pUC19 to yield pΔ35S(−90).

(c) p6AREΔADHGN and p6AREΔADHIGN

The construction of parent vectors, pADHCAT and pADHCAT140, is described in Walker et al. (1987) supra. The BamH1 fragment containing the Adh1 promoter (from position −1094 to position +106) was cloned upstream of the Adh1 intron 1 sequence in pIGN to produce pADHIGN. Truncated Adh1 promoter fragments spanning position −140 to position +106 were subcloned into pGN and pIGN from pADHCAT-140 to yield pΔADHGN and pΔADHIGN.

An anaerobic regulatory elements (ARE) (SEQ ID NO:3) is found between positions −140 and −99 of the maize Adh1 promoter. The ARE is composed of two sequence elements: Region I spanning positions −133 to −121 and Region II spanninq positions −113 and −99. An ARE was isolated as a Pst1 fragment (Walker et al. (1987) supra) and cloned upstream of the truncated Adh1 promoter in pΔADHIGN to yield pAREΔADHIGN. To reverse the orientation of the ARE, the Sal1 fragment from the polylinker (upstream of position −140) to position −99 in pAREΔADHIGN was cloned into the unique Sal1 site in pΔADHIGN, producing pARE(−)ΔADHIGN. Clones containing multiple ARE sequences (e.g., p2AREΔADHIGN, p4AREΔADHIGN, or p6AREΔADHIGN) were cloned as follows: pAREΔADHIGN was digested with Hincl1 and Pst1 linkers were added. The Pst1 fragment containing ARE from position −140 to −99 (SEQ ID NO:3) was then isolated and cloned back into pAREΔADHIGN, upstream of the Pst1 site (position −140). The number of repeated ARE sequences (SEQ ID NO:3) and their orientation were verified by nucleotide sequence analysis.

The plasmid p6AREΔADHGN was derived from p6AREΔADHIGN by replacement of the BamH1/Sac1 fragment containing Intron 1 of maize Adh1 and GUS by the BamH1/ Sac1 'GUS' fragment from p35SGN.

(d) p4OCSΔ35SIGN, p6ARE4OCSΔADHIGN and p6ARE4OCSΔ35SIGN constructs

Figure 1E:
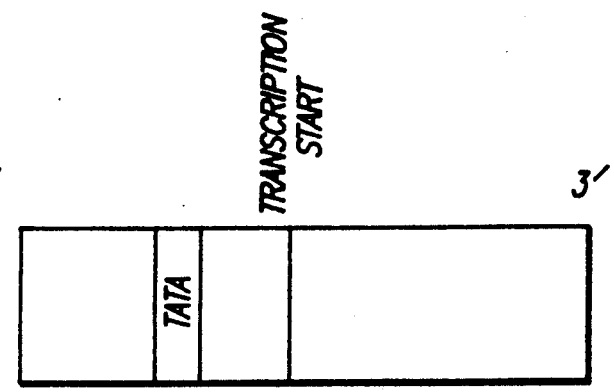
Figure 1E:
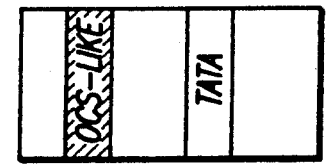
Figure 1E:
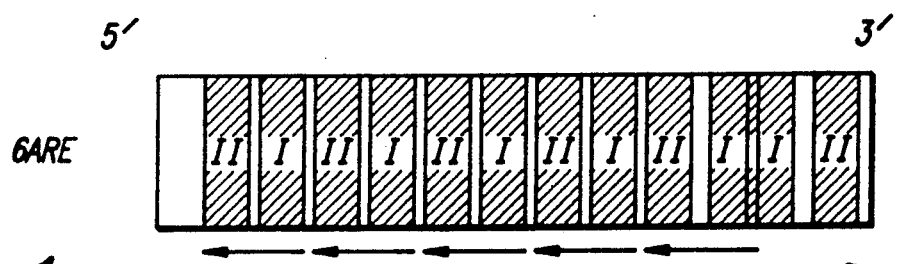
Figure 1F:
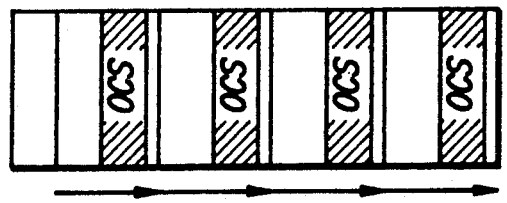

The OCS element was isolated as an EcoRI-BamHI fragment containing the HpaII (−292) to BamHI (−116) portion of the ocs upstream promoter region (DeGrene et al. (1982) J. Mol. Appl. Genet. 1:499-510) as described in Ellis et al. (1987) EMBO J. 6:11-16 and (1987) EMBO J. 6:3203-3208. A plasmid, p4OCSADH-CAT, containing four tandem copies of the ocs element (four 40-bp direct repeats of the −211 to −172 region from the ocs gene was prepared using the methods of Ellis et al. (1987) EMBO J. 6:3203-3208. The 4OCS element was prepared as a Sal1/Xho1 fragment p4OCSX, a derivative of p4OCSADHCAT into which of an Xho1 linker was inserted by ligation into the Sma1 site. The 4OCS element was added at the Sal1 site in pΔ35SIGN to give p4OCSΔ35SIGN and at the Sal1 site in p6AREΔADHIGN to give p6ARE4OCSΔADHIGN, both with the same orientation of the 4OCS array, as illustrated in FIG. 1e. The plasmid p6ARE-4OCSΔ35SIGN was derived from p6ARE4OCSΔAD-HIGN by replacing the Sal1/EcoR1 fragment containing 'ΔADHIGN' with the Sal1/EcoR1 fragment of pΔ35SIGN.

(e) p6AREΔ35SIGN and p6AREΔ35SGN constructs

The plasmid p6AREΔ35SIGN was derived from p6AREΔADHGN by replacing the Sal1/EcoR1 fragment containing 'ΔADHGN' with the Sal1/EcoR1 fragment from Δ35SIGN. The plasmid p6A-REΔ35SGN was derived from p6AREΔADHGN by replacing the Sal1/BamH1 'ΔADH' fragment with the Sal1/BamH1 fragment from pΔ35S(−90).

(f) Purification of Plasmid DNA

Plasmid DNA of the above constructs was prepared from *E. coli* JM109 (Yanisch-Perron et al. (1985) Gene 33:103-119) and purified by two rounds of centrifugation in CsCl gradients. The final preparations were resuspended at 1 mg/ml in 10 mM Tris-HCl, pH 8.0, 1 mM Na₂EDTA and aliquots were checked by DNA sequencing using a Pharmacia T7 kit and by the sizing of restriction fragments in a triple digestion with Hind111/Sal1/BamH1 and a double digestion with Pvu11/Sma1, to ensure that no sequence rearrangements had occurred. Only those preparations showing no spurious bands in gel electrophoresis were used in subsequent electroporations.

EXAMPLE 2

Plant cell culture and protoplast isolation

Protoplasts were isolated from the following cell lines. TM, an established line of einkorn (*Triticum monococcum*) (Koa et al. (1970) Can. J. Genet. Cytol. 12:297-301); BMS from *Zea mays* cv. Black Mexican Sweet (Chourey and Zurawski (1981) Theor. and Appl. Genet. 59:341-344); L1, a disomic addition line in the hexaploid wheat cultivar Vilmorin 27 containing two group 7 chromosomes from *Thinopyrum intermedium* in addition to the 42 wheat chromosomes, and produced by backcrossing a partial amphiploid hybrid between wheat and *Thinopyrum intermedium* to wheat (cv Vilmorin 27); LM, a line derived from endosperm of *Lolium multiflorum* (Smith and Stone (1973) Aust. J. Biol. Sci. 26:123-133); NpT₅ derived from a leaf protoplast culture *Nicotiana plumbaginifolia;* and ER, an embryonic culture of *Oryza sativa* cv. Taipei 309 initiated from immature embryos and maintained in liquid suspension culture for four months. The media used for the maintenance of the cell suspensions, the enzymes used for isolation of protoplasts, and the media used for protoplast culture were prepared as indicated in Table 4.

EXAMPLE 3

Electroporation of protoplasts

After complete digestion, protoplasts were sieved through 328, 110 and 50μm mesh sieves (twice through the 50 μm sieve in the case of the L1 and TM lines). Following sedimentation by slow speed centrifugation (80 g for 5 minutes), the protoplasts were resuspended in the washing solution found best suited to the particular cell type (see Table 1). The barley mesophyll protoplasts were washed in 0.375M mannitol, 10 mM MES, pH 5.8, 205 mM NaCl, 3.5 mM KCl, 9.4 mM MgSO₄, 8.4 mM MgCl₂, 3.4 CaCl₂, and 0.875 mM NaHCO₃.

The protoplasts were again sedimented, washed, sedimented and resuspended (Taylor and Larkin (1988) Austr. J. Biotech. 1:52-55) in TBS9 buffer (Tris 3.63 g/l, CaCl₂.2H₂O 876 mg/l, NaCl 8.78 mg/l, mannitol 50 g/l pH 9.0) at a concentration of $2 \times 10^6$ protoplasts/ml.

Immediately before electroporation, 200 μl of the protoplast suspension (100μl in the case of barley mesophyll) was added to a tube containing 5 μl of plasmid DNA dissolved in 5 μl of 10 mM Tris HCl, pH 8.0, 1 mM Na$_2$EDTA. The mixture was transferred to an electroporation chamber (2mm between electrodes) and three pulses of 275 V (1375 V/cm), with a pulse width of 5 ms and a delay of 100 ms, were applied between electrodes from a 24 μF capacitor (200 V was used in the case of the barley mesophyll protoplasts). After allowing the protoplasts to recover for 5 seconds, the protoplast suspension was pipetted back into a microfuge tube to which 600 μl washing solution was added. The tubes were spun gently (<100 g) for 5 minutes, the supernatant removed and the protoplasts resuspended in 1 ml of culture medium. The protoplast suspensions were transferred to 35 mm petri dishes which were sealed in parafilm and incubated at 25° C. in the dark to allow expression of the GUS gene.

EXAMPLE 4

Assay of GUS gene expression in electroporated protoplasts

After incubation for 44 to 48 hours, 400 μl washing solution was added to each dish and each protoplast sample was gently pipetted into a microfuge tube. The tubes were centrifuged at 100 g for 8 minutes and the supernatant was discarded. Protoplast pellets were either stored at −80° C. until required or used immediately. Each pellet was resuspended, with the aid of a vortex mixer, in 250 μl extraction buffer (Jefferson et al. (1987) supra). The samples were sonicated on ice for 5 seconds using a Labsonic 1510 sonicator set at 55W, equipped with a microtip probe. Debris was pelleted by centrifugation in a microfuge for 1 minute and the clear supernatant was assayed for total protein using a Bio-Rad kit according to the manufacturers' recommendations. For each set of constructs the fluorometric GUS assay (Jefferson et al. (1987) supra) was performed on an aliquot of the supernatant containing a fixed amount of total protein in the range of 5 to 50 μg dissolved in 100 μl lysis buffer. A further 100 μl extraction buffer containing 2 mM 4-methyl-umbelliferyl-β-D-glucuronide (MUG) was added, the mixture was vortexed briefly and incubated at 37° C. for a fixed time in the range of 20 to 160 minutes. The reaction was stopped by the addition of 1000 μl 0.2M Na$_2$CO$_3$ and fluorescence at 455 nm was measured using a Perkin-Elmer Spectrofluorimeter set at an excitation wavelength of 365 nm.

EXAMPLE 5

Preparation of Solutions and Media

Culture medium CM1 is the CS5 medium described by Scowcroft and Adamson (1976, Plant Sci. Lett. 7:39–42) with the pH adjusted to 5.8. CM2 contains the mineral salts of Murashige and Skoog (1962, Physiol. Plant. 15:473–497), 170mg/l L-asparagine, 0.77 mg/l glycine, 0.13 mg/l nicotinic acid, 0.025 mg/l calcium pantothenate, 0.025 mg/l thiamine.HCl, 0.025mg/l pyridoxine.HCl, 4 mg/l 2,4-dichlorophenoxyacetic acid (2,4-d), 20 g/l sucrose, pH5.8. CM3 is WtM1 (Young et al., 1989, J. Gen. Virol. 70:2245–2251). CM4 contains the major inorganic salts of White (1963, in *The cultivation of animal and plant cells*, 2nd ed., Ronald Press, New York), the minor salts and vitamins of Murashige and Skoog (1962, supra), 100 mg/l myo-inositol, 5/gl yeast extract, 10 mg/l ferric citrate, 1 mg/l indole-3-acetic acid (IAA), 40 g/l sucrose, pH5.5. CM5 contains the major and minor inorganic elements of R2 medium (Ohira et al., 1973, Plant Cell Physiol. 14:1113–1121) with 9 mg/l FeCl$_3$, 11.2 mg/l Na$_2$EDTA, 1 mg/l thiamine.HCl, 2mg/l 2,4-D, 20 g/l sucrose, pH5.9.

Protoplast washing solution PW1 consists of 0.3M mannitol, 156 mM NaCl, 3.5 mM KCl, 9.4 mM MgSO$_4$, 8.4 mM MgCl$_2$, 3.4 mM CaCl$_2$, 0.9 mM NaHCO$_3$, pH6.0. PW2 contains the major and minor mineral salts of B5 medium (Gamborg et al. (1968) Exp. Cell Res. 50:151–158), 27 mM mannitol, 109 mM KCl, 105 mM MgCl$_2$, 33 mM CaCl$_2$, 3 mM 2-(N-morpholino) ethanesulphonic acid (MES), pH5.7. PW3 consists of 0.568 M mannitol, 80 mM CaCl$_2$, 0.2% MES, pH5.8. PW4 is PW2 with the concentration of mannitol raised to 49 mM.

Enzyme digestion mixture ED1 consists of 1% (w/v) Cellulysin (Calbiochem), 1% (w/v) Driselase, 1% (w/v) Macerozyme (Onozuka R-10) in washing solution PW1 with the pH adjusted to 5.8. ED2 contains 1% (w/v) Cellulysin (Calbiochem), 0.5% (w/v) Hemicellulase (Sigma), 0.02% Pectolyase Y-23 (Seishin Pharmaceutical), 50 mM CaCl$_2$, 10 mM sodium acetate, 0.2M mannitol, pH5.8. ED3 contains 1% (w/v) Cellulase RS (Yakult Honsha), 0.1% (w/v) Driselase, 0.06% (w/v) Pectolyase Y-23, 0.2% (w/v) Hemicellulase, 0.2% (w/v) Macerozyme R-10, 0.495M mannitol, 0.189M glucose, 2 mM ascorbic acid, 14 mM CaCl$_2$, 3 mM MES, pH5.8 ED4 is 0.5% (w/v) Cellulase RS, 0.68% (w/v) Driselase, 0.05% Pectolyase Y-23, 6.5 mM MES, 0.325M mannitol, 40 mM CaCl$_2$, to which 0.5% (w/v) activated charcoal was added. After gentle agitation for 30 minutes, the charcoal was removed by centrifugation at 10,000g. The solution was then adjusted to pH5.9 and sterilized by filtration. ED5 is 1% (w/v) Cellulase RS, 0.1% (w/v) Driselase, 0.1% (w/v) Pectolyase Y-23, 0.35M mannitol, 3 mM MES, pH5.9.

The protoplast culture media were all sterilized by filtration before use. Protoplast culture medium PC1 consists of the medium of Kao and Michayluk (1975) Planta 126:105–110 without the free amino acids, adenine, guanine, thymine, uracil, hypoxanthine, xanthine, riboflavin and vitamin B12, as suggested by Vasil and Vasil (1980) Theor. Appl. Gen. 56:97–99, but containing 0.4M glucose, 0.1M sucroase, 1mg/l 2,4-D, 0.2 mg/l zeatin, pH adjusted to 5.6. The medium was ultrafiltered through an Amicon YM10 membrane (Davies et al. (1980) Plant Sci. 60:237–244) prior to filter sterilization. PC2 consists of the inorganic elements of Murashige and Skoog (1962, supra), 7.7 mg/l glycine, 1.3 mg/l nicotinic acid, 0.25 mg/l thiamine.HCl, 0.25 mg/l pyridoxine.HCl, 0.25mg/l calcium pantothenate, 167 mg/l L-asparagine, 1 g/l L-glutamine, 66 g/l mannitol, 20 g/l sucrose, 1.67 g/l glucose, 2% (v/v) coconut water (Gibco), 4 mg/l 2,4-D and 0.1 mg/l 6-benzylaminopurine, pH5.8. PC3 consists of the major and minor minerals of Kao and Michayluk (1975, supra), 1 mg/l nicotinamide, 1 mg/l pyridoxine.HCl, 1 mg/l thiamine.HCl, 1 mg/l calcium pantothenate, 0.4 mg/l folic acid, 0.02 mg/l p-aminobenzoic acid, 0.01 mg/l biotin, 400 mg/l m-inositol, 2% (v/v) coconut water, 750 mg/l casein hydrolysate, 200 mg/l L-glutamine, 150 mg/l L-aspartic acid, 10 g/l sucrose, 108 g/l glucose, 1 mg/l 2,4-D, 0.2 mg/l 1-naphthaleneacetic acid, 0.2 mg/l zeatin, pH5.6. PC4 is CM4 with the addition of 73 g/l sorbitol. PC5 has the inorganic ingredients of CM5 plus the vitamins of B5 medium (Gamborg et al., 1968, supra), the sugars and organic acids of Kao (1977, Mol. Gen. Genet. 150:225-230), 137 g/l sucrose, 2 mg/l 2,4-D and 0.1 mg/l kinetin, pH5.7.

TABLE 1

Expression of the GUS gene in different plant cell lines, relative to the GUS expression obtained using p35SGN

| Plant | Nicotiana | Maize | Wheat | Einkorn | Lolium | Rice |
|---|---|---|---|---|---|---|
| Name of cell line | NpT5 | BMS | L1 | TM | LM | ER |
| Number of replicates | 7 | 8 | 5 | 6 | 7 | 5 |
| Construct | | | | | | |
| pGN | 0.004 | 0.026 | 0.000 | 1.6 | 0.17 | 0.000 |
| PIGN | 0.001 | 0.18 | 1.3 | 2.4 | 2.4 | 4.8 |
| PΔ35SGN | 0.69 | 1.1 | 0.10 | 1.2 | 0.16 | 6.2 |
| pΔ35SIGN | 1.7 | 2.2 | 0.59 | 1.2 | 0.39 | 4.2 |
| p4OCSΔ35SIGN | 8.4 | 6.1 | 0.088 | 2.3 | 3.9 | 6.5 |
| p6AREΔADHGN | 0.17 | 1.1 | 0.76 | 2.7 | 0.40 | 0.98 |
| p6AREΔADHIGN | 0.048 | 8.2 | 18 | 9.3 | 0.55 | 14 |
| p6AREΔ35SGN | 0.53 | 8.2 | 0.49 | 1.2 | 0.11 | 0.8 |
| p6ARE 35SIGN | 2.0 | 5.2 | 1.3 | 1.0 | 0.65 | 1.4 |
| p6ARE4OCSΔADHIGN (pEmuGN) | 0.83 | 41 | 40 | 20 | 8.8 | 25 |
| p35SGN | 1 | 1 | 1 | 1 | 1 | 1 |
| p35SIGN | 1.2 | 1.6 | 0.59 | 1.2 | 0.5 | 1.3 |

TABLE 2

Mean specific activity (picomoles 4MU/mg protein/min.) with Standard Errors shown in brackets

| Construct | p35SGN | | p6ARE4OCSΔADHIGN (pEmuGN) | | p4OCSΔ35SIGN | |
|---|---|---|---|---|---|---|
| Cell line | | | | | | |
| Nicotiana NpT5 | 157 | (72) | 131 | (49) | 1312 | (600) |
| maize BMS | 17 | (9.7) | 698 | (365) | 103 | (48) |
| wheat L1 | 0.68 | (0.38) | 27 | (5.4) | 0.06 | (0.06) |
| einkorn TM | 0.41 | (0.17) | 8 | (1.4) | 0.94 | (0.30) |
| Lolium LM | 1.7 | (1.2) | 15 | (5.0) | 6.6 | (2.3) |
| rice ER | 0.69 | (0.19) | 17 | (3.2) | 4.5 | (2.1) |
| Tissue | | | | | | |
| barley mesophyll | 0.21 | (0.21) | 0.21 | (0.21) | 16 | (1.0) |

4MU = 4-methyl umbelliferone

Standard Error = $S = \sqrt{\frac{\Sigma y^2}{n}}$ where
y = specific activity value obtained and
n = number of values obtained
Specific activities of β-glucuronidase (GUS) in protoplast extracts following transient expression of p35SGN, p6ARE4OCSΔADHIGN and p4OCSΔ35SIGN. The barley mesophyll protoplasts required slightly different electroporation conditions as specified in Example 3.

TABLE 3

Mean specific activity (picomoles of 4 MU/mg protein/min.)

| Construct | Aerobic | | Anaerobically induced | |
|---|---|---|---|---|
| p6AREΔADHIGN | 1.4 | [0.73]* | 4.3 | [1.3] |
| p6AREΔ35SIGN | 0 | | 0.21 | [0.04] |
| p6ARE4OCSΔADHIGN | 29.3 | [6.7] | 28.7 | [4.5] |

Expression obtained using three different constructs under aerobic or anaerobic conditions.
*Standard errors are shown in brackets

TABLE 4

Media used in the preparation of protoplasts from the cell lines. The composition of the media is detailed in the text.

| Plant | Nicotiana | Maize | Wheat | Einkorn | Lolium | Rice |
|---|---|---|---|---|---|---|
| Name of cell line | NpT5 | BMS | L1 | TM | LM | ER |
| Cell suspension culture medium | CM1 | CM2 | CM3 | CM3 | CM4 | CM5 |
| Enzyme digestion mixture | ED1 | ED2 | ED3 | ED3 | ED4 | ED5 |
| Protoplast washing solution | PW1 | PW2 | PW3 | PW3 | PW1 | PW4 |
| Protoplast culture medium | PC1 | PC2 | PC3 | PC3 | PC4 | PC5 |

We claim:

1. A recombinant promoter molecule, useful for enhancing expression of a plant-expressible structural gene in a monocot plant cell, said promoter molecule comprising:

(a) a plurality of enhancer elements selected from the group consisting of only ARE elements, only OCS elements, and combinations of ARE and OCS elements;

(b) a truncated, plant expressible promoter, providing a TATA box region and a transcription start site, said promoter selected from the group consisting of Δ35S and ΔADH positioned 3' to said plurality of enhancer elements wherein said truncated promoter excludes the presence of enhancer sequences and wherein said truncated promoter is recombined with said plurality of enhancer elements positioned 5' to said truncated promoter; and (c) a maize Adh1 intron positioned 3' to said transcription start site whereby a plant-expressible structural gene, placed 3' to said recombinant promoter molecule, is expressed in said monocot plant cell under regulatory control of said recombinant promoter molecule.

2. The recombinant promoter molecule of claim 1 having the structure 4OCSΔ35SI where 4 OCS refers to 4 tandemly repeated copies of OCS each OCS having the nucleotide sequence as shown in SEQ ID:1, Δ35S is a truncated CAMV 35S promoter having the nucleotide sequence as shown in SEQ ID:2, and I is the Adh1 intron, having the nucleotide sequence as shown in SEQ ID:5.

3. The recombinant promoter molecule of claim 1 having the structure 6AREΔADHI, wherein 6ARE refers to 6 tandemly repeated copies of ARE, each ARE having the nucleotide sequence as shown in SEQ ID:3, ΔADH is a truncated Adh1 promoter having the nucleotide sequence shown in SEQ ID:4, and I is the Adh1 intron having the nucleotide sequence shown in SEQ ID:5.

4. The recombinant promoter molecule of claim 1 having the structure 6ARE4OCSΔADHI, wherein 6 ARE refers to 6 tandemly repeated copies of ARE, each ARE having the nucleotide sequence as shown in SEQ ID:3, 4OCS refers to 4 tandemly repeated copies of OCS, each OCS having the nucleotide sequence as shown in SEQ ID:1, ΔADH is a truncated Adh promoter, and I is the Adh1 intron having the nucleotide sequence as shown in SEQ ID:5.

5. A vector comprising said recombinant promoter molecule of claim 1.

6. A bacterial cell containing the vector of claim 5.

7. A transformable, regenerable monocot plant transformed to comprise the recombinant promoter molecule of claim 1 and a plant-expressible structural gene placed 3' to said recombinant promoter molecule such that said structural gene is expressed under control of said recombinant promoter molecule.

8. A plant of claim 7 selected from the group consisting of maize, wheat, barley, and rice.

9. A transformable, regenerable monocot plant cell transformed to comprise the recombinant promoter molecule of claim 1 and a plant-expressible structural gene placed 3' to said recombinant promoter molecule such that said structural gene is expressed under control of said recombinant promoter molecule.

10. A maize cell of claim 9.

11. A wheat cell of claim 9.

12. A barley cell of claim 9.

13. A rice cell of claim 9.

14. The recombinant promoter molecule of claim 1 wherein said ARE elements have the nucleotide sequence disclosed in SEQ ID NO:3.

15. The recombinant promoter molecule of claim 1 wherein said OCS elements have the nucleotide sequence disclosed in SEQ ID NO:1.

16. The recombinant promoter molecule of claim 1 wherein said Δ35S promoter has the nucleotide sequence disclosed in SEQ ID NO:2.

17. The recombinant promoter molecule of claim 1 wherein said ΔADH promoter has the nucleotide sequence disclosed in SEQ ID NO:4.

18. The recombinant promoter molecule of claim 1 wherein said Adh1 intron has the nucleotide sequence disclosed in SEQ ID NO:5.

* * * * *

UNITED STATES PATENT AND TRADEMARK OFFICE
CERTIFICATE OF CORRECTION

PATENT NO. : 5,290,924                          Page 1 of 2

DATED : March 1, 1994

INVENTOR(S) : Last *et al.*

It is certified that error appears in the above-identified patent and that said Letters Patent is hereby corrected as shown below:

Column 1, line 44: Delete "about 35 bp" and insert --about —35 bp--.
Column 2, line 18: Delete "(dennis" and insert --(Dennis--.
Column 2, line 52: Delete "Arabidoosis" and insert --Arabidopsis--.
Column 3, line 10: Delete "to 31 90," and insert --to —90--.
Column 3, line 64: Delete "(Singh al and insert --(Singh *et al.*--.
Column 5, line 46: After "Adh1 gene" insert --SEQ ID: 5--.
Column 8, line 39: After "+3" insert --SEQ ID: 2--.
Column 9, line 5: Delete "The OCS element" and insert --The 16 bp sequence--.
Column 10, line 67: After "(T/C)AAG" delete the extra spaces.
Column 11, line 15: After "roots" insert --,--.
Column 12, line 60: After "Adh1 Intron 1" insert --SEQ ID: 5--.
Column 14, line 12: Delete "(p4OCS'35SGN)" and insert --(p4OCSΔ35SGN)--.
Column 15, line 27: Delete "68: Wu" and insert --68; Wu--.
Column 16, line 68: Delete "(nucleot 7665)" and insert --(nucleotide 7665)--.
Column 17, line 17: Delete "regulatory elements" and insert --regulatory element--.
Column 17, line 21: Delete "to —121" and insert --to —124--.
Column 17, line 52: Delete "(DeGene" and insert --(DeGreve--.
Column 17, line 55: Delete "ocs" and insert --OCS--.

UNITED STATES PATENT AND TRADEMARK OFFICE
CERTIFICATE OF CORRECTION

PATENT NO.    : 5,290,924

DATED         : March 1, 1994

INVENTOR(S)   : Last *et al.*

It is certified that error appears in the above-identified patent and that said Letters Patent is hereby corrected as shown below:

Column 19, line 61: Delete "thiamine . HCL" and insert --thiamine · HCL--.
Column 19, line 62: Delete "pyridoxin . HCL" and insert --pyridoxin · HCl
Column 20, line 6: Delete "thiamine . HCL" and insert --thiamine · HCl
Column 20, line 40: Delete "PCI" and insert --PC1--.
Column 20, line 53: Delete "thiamine . HCL" and insert --thiamine · HCL--.
Column 20, line 54: Delete "pyridoxine . HCL" and insert --pyridoxine · HCL--.
Column 20, line 60: Delete "pyridoxine . HCL" and insert --pyridoxine · HCL--.
Column 20, line 61: Delete "thiamine . HCL" and insert --thiamine · HCL--.
column 29, line 14: Delete "intron positioned" and insert --intron, as shown in SEQ ID: 5, positioned--.

Signed and Sealed this

Fourth Day of October, 1994

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Agrobacterium Tumefaciens ( x ) PUBLICATION INFORMATION:
        ( A ) AUTHORS: DeGreve, et al.,
        ( B ) TITLE: Nucleotide Sequence and Transcript Map of the
            Agrobacterium Tumeficiens Ti Plasmid-Encoded
            Octopine Synthase Gene
        ( C ) JOURNAL: J. Mol. Appl. Genet.
        ( D ) VOLUME: 1
        ( F ) PAGES: 499-510
        ( G ) DATE: 1982

( x i ) SEQUENCE DESCRIPTION: SEQ ID NO:1:

```
CCTCAAGGGT CCACCAAAAA CGTAAGCGCT TACGTACATG                    40
```

( 2 ) INFORMATION FOR SEQ ID NO:2:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Cauliflower mosaic virus ( x ) PUBLICATION INFORMATION:
        ( A ) AUTHORS: Fang, et al.,
        ( B ) TITLE: Multiple Cis Regulatory Elements for Maximal
            Expression of the Cauliflower Mosaic Virus 35S
            Promoter in Transgenic Plants
        ( C ) JOURNAL: Plant Cell
        ( D ) VOLUME: 1
        ( F ) PAGES: 141-150
        ( G ) DATE: 1989

( x i ) SEQUENCE DESCRIPTION: SEQ ID NO:2:

```
TCTCCACTGA CGTAAGGGAT GACGCACAAT CCCACTATCC TTCGCAAGAC CCTTCCTCTA    60
TATAAGGAAG TTCATTTCAT TTGGAGAG                                        88
```

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Zea Mays ADH1

(x) PUBLICATION INFORMATION:
    (A) AUTHORS: Blocker, et al.,
    (B) TITLE: DNA Sequences Required for Anaerobic
        Expression of the Mays Alcohol Dehydrogenase 1
        Gene
    (C) JOURNAL: Proc. Natl. Acad. Sci. U.S.A.
    (D) VOLUME: 84
    (F) PAGES: 6624-6628
    (G) DATE: 1987

(x i) SEQUENCE DESCRIPTION: SEQ ID NO:3:

CTGCAGCCCC GGTTTCGCAA GCCGCGCCGT GGTTTGCTTG CC    42

(2) INFORMATION FOR SEQ ID NO:4:

(i) SEQUENCE CHARACTERISTICS:
    (A) LENGTH: 105 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Zea Mays ADH1

(x) PUBLICATION INFORMATION:
    (A) AUTHORS: Dennis, et al.,
    (B) TITLE: Molecular Analysis of the Alcohol
        Dehydrogenase (ADH1) Gene of Maize
    (C) JOURNAL: Nucleic Acids Res.
    (D) VOLUME: 126
    (F) PAGES: 3983-4000
    (G) DATE: 1984

(x i) SEQUENCE DESCRIPTION: SEQ ID NO:4:

CCCACAGGAT CTCGCTTTGG ATCGATTGGT TTCGTAACTG GTGAAGGACT GAGGGTCTCG    60

GAGTGGATCG ATTTGGGATT CTGTTCGAAG ATTTGCGGAG GGGGG    105

(2) INFORMATION FOR SEQ ID NO:5:

(i) SEQUENCE CHARACTERISTICS:
    (A) LENGTH: 554 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Zea Mays ADH1

(x) PUBLICATION INFORMATION:
    (A) AUTHORS: Dennis, et al.,
    (B) TITLE: Molecular Analysis of the Alcohol
        Dehydrogenase (ADH1) Gene of Maize
    (C) JOURNAL: Nucleic Acids Res.
    (D) VOLUME: 12
    (F) PAGES: 3983-4000
    (G) DATE: 1984

( x i ) SEQUENCE DESCRIPTION: SEQ ID NO:5:

| | | | | | |
|---|---|---|---|---|---|
| TGATCAAGTG | CAAAGGTCCG | CCTTGTTTCT | CCTCTGTCTC | TTGATCTGAC | TAATCTTGGT | 60
| TTATGATTCG | TTGAGTAATT | TTGGGGAAAG | CTTCGTCCAC | AGTTTTTTTT | TCGATGAACA | 120
| GTGCCGCAGT | GGCGCTGATC | TTGTATGCTA | TCCTGCAATC | GTGGTGAACT | TATGTCTTTT | 180
| ATATCCTTCA | CTACCATGAA | AAGACTAGTA | ATCTTTCTCG | ATGTAACATC | GTCCAGCACT | 240
| GCTATTACCG | TGTGGTCCAT | CCGACAGTCT | GGCTGAACAC | ATCATACGAT | ATTGAGCAAA | 300
| GATCTATCTT | CCCTGTTCTT | TAATGAAAGA | CGTCATTTTC | ATCAGTATGA | TCTAAGAATG | 360
| TTGCAACTTG | CAAGGAGGCG | TTTCTTTCTT | TGAATTTAAC | TAACTCGTTG | AGTGGCCCTG | 420
| TTTCTCGGAC | GTAAGGCCTT | TGCTGCTCCA | CACATGTCCA | TTCGAATTTT | ACCGTGTTTA | 480
| GCAAGGGCGA | AAAGTTTGCA | TCTTGATGAT | TTAGCTTGAC | TATGCGATTG | CTTTCCTGGA | 540
| CCCGTGCAGC | TGCG | | | | | 554

( 2 ) INFORMATION FOR SEQ ID NO:6:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Agrobacterium Tumefaciens OCS ( x ) PUBLICATION INFORMATION:
( A ) AUTHORS: Ellis, et al.,
( B ) TITLE: The OCS Element: A Sixteen Base Pair
Palindrome Essential for Activity of the Octopine
Synthase Enhancer
( C ) JOURNAL: EMBO J.
( D ) VOLUME: 6
( F ) PAGES: 3203-3208
( G ) DATE: 1987

( x i ) SEQUENCE DESCRIPTION: SEQ ID NO:6:

ACGTAAGCGC TTACGT                                                                                      16

( 2 ) INFORMATION FOR SEQ ID NO:7:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Agrobacterium Tumefaciens OCS ( x i ) SEQUENCE DESCRIPTION: SEQ ID NO:7:

TGACGYAAGS RMTKACGYMM                                                                                  20